United States Patent

Ashikari et al.

[11] Patent Number: 5,965,444
[45] Date of Patent: Oct. 12, 1999

[54] METHOD FOR CONSTRUCTING TRANSFORMANT NOT HAVING SELECTIVE MARKER GENE

[75] Inventors: Toshihiko Ashikari, Takatsuki; Hiroto Kondo, Fuchu; Keiko Sakakibara, Muko; Hiroyuki Araki, Minoo; Yasuji Oshima, Takatsuki, all of Japan

[73] Assignee: Suntory Limited, Osaka, Japan

[21] Appl. No.: 08/880,745

[22] Filed: Jun. 23, 1997

[30]     Foreign Application Priority Data

Jun. 21, 1996 [JP] Japan .................................. 8-179820

[51] Int. Cl.⁶ .............................. C12Q 1/68; C07H 21/04
[52] U.S. Cl. .......................... 435/483; 435/471; 435/476; 435/477; 435/320.1; 536/23.2; 536/23.7
[58] Field of Search ..................... 435/471, 476, 435/477, 483, 320.1; 536/23.2, 23.7

[56]            References Cited

U.S. PATENT DOCUMENTS

| | | | |
|---|---|---|---|
| 5,122,465 | 6/1992 | Cregg et al. | 435/172.3 |
| 5,441,884 | 8/1995 | Baum | 435/252.31 |
| 5,658,772 | 8/1997 | Odell et al. | 435/172.3 |

FOREIGN PATENT DOCUMENTS

97/37012  10/1997  WIPO .

OTHER PUBLICATIONS

Senecoff et al., J. Mol. Biol. 201, 405–421, 1988.
Matsuzaki et al., Biosci. Biotech. Biochem. 58(9), 1632–1637, 1994.
Cregg et al., Mol. Gen. Genet. 219, 320–323, 1989.
Fiering et al., Proc. Natl. Acad. Sci. USA 90, 8469–8473, 1993.
Sauer, Bio Techniques 16(6), 1086–1088, 1994.
J.T. Odell et al., "Use Of Site–Specific Recombination Systems In Plants," *Homologous Recombination and Gene Silencing in Plants,* 1994, pp. 219–270.
H. Albert et al., "Site–Specific Integration Of DNA Into Wild–Type And Mutant lox Sites Placed In The Plant Genome," *The Plant Journal,* vol. 7, No. 4, 1995, pp. 649–659.
H. Onouchi et al., "Visualization Of Site–Specific Recombination Catalyzed By A Recombinase From *Zygosaccharomyces rouxii* In *Arabidopsis thliana,*" *Mol. Gen. Genet,* vol. 247, 1995, pp. 653–660.
N. Kilby et al., "FLP Recombinase In Transgenic Plants: Constitutive Activity In Stably Transformed Tobacco And Generation Of Marked Cell Clones In Arabidopsis," *The Plant Journal,* vol. 8, No. 5, 1995, pp. 637–652.

*Primary Examiner*—Kenneth R. Horlick
*Attorney, Agent, or Firm*—Burns, Doane, Swecker & Mathis, L.L.P.

[57]            ABSTRACT

A DNA construct wherein a DNA fragment which is recombinable in yeast chromosomal DNA is directly or indirectly linked at both ends of a DNA fragment which comprises a pair of R sensitive sequences oriented in the same direction and flaking both an R gene placed under the control of an inducible promoter and an expressible selective marker gene, which is a DNA construct designed with the R sensitive sequences non-symmetrically shortened, so that no functionable R sensitive sequence remains after the R sensitive sequence recombination has occurred by expression of the R gene and the selective marker has been removed. Since no functionable R sensitive sequence remains after removal of the selective marker, recombination does not occur again, and thus the same selective marker may be used for multiple insertions of foreign genes.

10 Claims, 12 Drawing Sheets

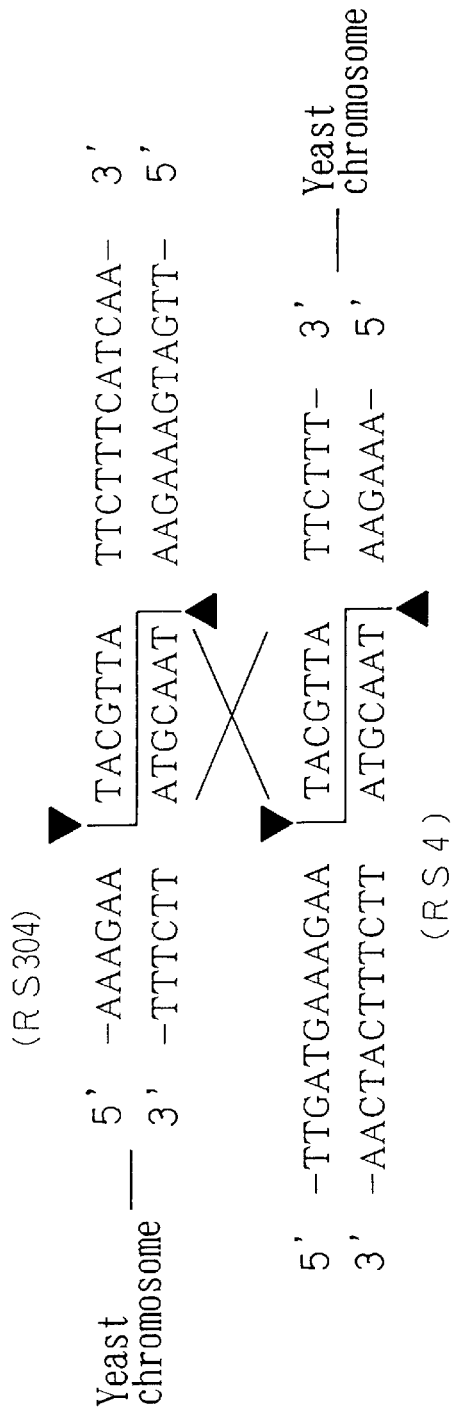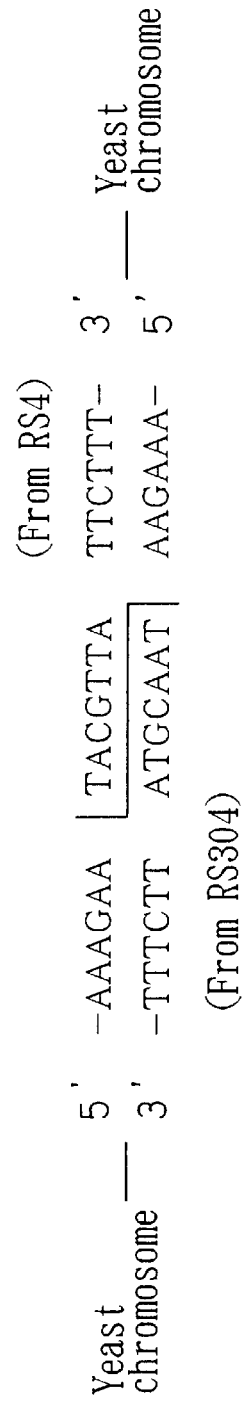
Fig. 10

```
                           SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
           (A) LENGTH: 31 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:1:

TTGATGAAAG AATACGTTAT TCTTTCATCA A                                 31

(2) INFORMATION FOR SEQ ID NO:2:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:2:

TTGATGAAAG AATACGTTAT TCTTTCATC                                    29

(2) INFORMATION FOR SEQ ID NO:3:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:3:

TTGATGAAAG AATACGTTAT TCTTTCA                                      27

(2) INFORMATION FOR SEQ ID NO:4:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:4:

TTGATGAAAG AATACGTTAT TCTTT                                        25
```

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
AAAGAATACG TTATTCTTT                                              19
```

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
TTGATGAAAG AATACGTTAT TCT                                         23
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
TTGATGAAAG AATACGTTAT T                                           21
```

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
TTGATGAAAG AATACGTTA                                              19
```

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
TTGATGAAAG AATACGTTAT CTTTCATCAA                                  30
```

(2) INFORMATION FOR SEQ ID NO:10:

(i) SEQUENCE CHARACTERISTICS:
        (A) LENGTH: 28 base pairs
        (B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO:10:

TTGATGAAAG AATAGTTATT CTTTCATC                                          28

(2) INFORMATION FOR SEQ ID NO:11:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

TTGATGAAAT AATACGTTAT TCTTT                                             25

(2) INFORMATION FOR SEQ ID NO:12:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

TTGATGAAAG AATACGTTAT TCTTTCATCA A                                      31

(2) INFORMATION FOR SEQ ID NO:13:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

CTTGATGAAA GAATACGTTA TTCTTTG                                           27

(2) INFORMATION FOR SEQ ID NO:14:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

AATTCAAAGA ATAACGTATT CTTTCATCAA GAGCT                                  35

(2) INFORMATION FOR SEQ ID NO:15:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO:15:

CTTGATGAAA GAATAACGTA TTCTTTA     27

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AGCTTAAAGA ATACGTTATT CTTTCATCAA GCATG     35

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CTTGATGAAA GAATACGTTA TTCTTTCA     28

(2) INFORMATION FOR SEQ ID NO:18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

AATTCTGAAA GAATAACGTA TTCTTTCATC AAGAGCT     37

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CTTGATGAAA GAATAACGTA TTCTTTCA     28

(2) INFORMATION FOR SEQ ID NO:20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

AGCTTGAAAG AATACGTTAT TCTTTCATCA AGCATG     36

METHOD FOR CONSTRUCTING TRANSFORMANT NOT HAVING SELECTIVE MARKER GENE

BACKGROUND OF INVENTION

1. Field of Invention

The present invention relates to a method for preparing a transformant lacking the selective marker gene, by site-specific recombination in yeast. The method of the invention may be used to obtain yeast transformants having no selective marker genes after introduction of a target gene into yeast.

2. Related Art

A number of gene introduction methods have been reported to date, all of which require markers for selection of recombinants because of low efficiency of gene introduction. Selective markers include those which revive prototrophy from auxotrophy when used in yeast, but usually resistance genes against drug agents such as antibiotics are used. However, the selective marker genes are preferably removed after selection of the transformants, for reasons of safety of the recombinants in practical use. Furthermore, due to the scarcity of selective markers which can be efficiently used, the marker genes are preferably reused for repeated transformation of the same individuals.

In order to overcome these problems there have been developed a few methods for removing selective marker genes from transformants. For example, in methods such as the co-transformation method, a gene to be introduced and a selective marker gene are placed on separate plasmids or DNA fragments and introduced simultaneously into a cell as separate constructs. According to this method, each of the genes exists independently and therefore it is possible to obtain individuals among the progeny which have the introduced target gene but lack the selective marker gene.

Methods utilizing transposons have also been developed. These methods rely on the action of transposons after gene introduction, to eliminate the link between the introduced target gene and the selective marker gene to allow obtainment of individuals among the progeny which have the introduced target gene but lack the selective marker gene, similar to the preceding method. However, these methods require generation of progeny, which causes the procedures to be complicated and time-consuming. In addition, variability is also produced among the progeny, thus lowering the practical usefulness.

On the other hand, methods utilizing site-specific recombination have also been developed. Site-specific recombination involves 2 elements, namely the enzyme which carries out recombination and a specific nucleotide sequence recognized by the enzyme, and recombination enzymes are known to induce recombination between 2 recognized sequences. Such recombination induces such phenomena as deletions, insertions and inversions, depending on the arrangement of recognized sequence. The four site-specific recombinants known are bacteriophage P1-derived Cre/lox, *Saccharomyces cerevisiae*-derived FLP/FRT, *Zygosaccharomyces rouxii*-derived R/RS and bacteriophage Mu-derived Gin/gix.

A great number of site-specific recombinations have been reported using these systems (Odell, J. T. and Russell, S. H., In: Paszkowski (ed.) Homologous Recombination and Gene Silencing in Plants, pp.219–270, 1994, Kluwer Academic Publishers, Netherlands; Yoder, J. I. and Goldsbrough A. P., Bio/Technology, 12, 263–267, 1994). For example, a *Saccharomyces cerevisiae* FLP/FRT system has been used, wherein the marker gene is removed with methylotrophic yeast (*Pichia pastoris*) (Cregg, J. M. and Madden, K. R., Mol. Gen. Genet. 219, 320–323, 1989).

The above authors used the ARG4 gene as a selective marker, and incorporated the ARG4 gene into a repeating FRT sequence in the same direction, to transform an arg4 mutant of methylotrophic yeast. A plasmid containing the recombinant enzyme gene FLP was then introduced into the same methylotrophic yeast to induce a site-specific recombination, by which the ARG4 selective marker gene was successfully removed. Although the ability to utilize site-specific recombination in this manner for removing markers had already been reported, as is clear from the example of Cregg et al., the method adopted for inducing the site-specific recombination is to introduce the recombination enzyme gene after the first transformants to induce the site-specific recombination.

In other words, two transformations are necessary for the induction, and therefore two separate selective markers are also necessary. Other reported site-specific recombinations also involve introduction of the recombination enzyme gene after obtaining the first transformants, and thus it is essential to introduce the recombination enzyme gene by a second transformation or by hybridization.

Araki et al. have demonstrated that a mechanism for site-specific recombination exists on the *Zygosaccharomyces rouxii* plasmid pSR1 (Araki, H. et al., J. Mol. Biol., 182, 191–203, 1985).

Plasmid pSR1 is a circular plasmid of 6251 bp, which is known to have a pair of inverted repeats with 959 bp in the molecule, with the site-specific recombination occurring between the inverted repeats. The recombination site in the inverted repeat consists of a 7 bp spacer sequence between short inverted repeats of 12 bp and 4 identical 12 bp sequences continue to repeat on one side. The site-specific recombination occurs when the recombination-performing enzyme (R protein) encoded in the plasmid itself binds to the R sensitive sequence, which is a specific nucleotide sequence on the recombination site in the inverted repeat.

A 31 bp sequence comprising a 7 bp-spacer portion and two 12 bp inverted repeats is known as an R sensitive sequence (RS sequence) (Matsuzaki, H. et al., Biosci. Biotech. Biochem., 58, 1632–1637, 1994). This sequence is listed as SEQ ID No.1. However, using the 31 bp R sensitive sequence for site-specific recombination is impractical since the structure after recombination includes the recognition site of the site-specific enzyme remaining in the chromosomal or plasmid DNA, which may induce unwanted recombination.

SUMMARY OF INVENTION

Here, the present inventors have set forth with the object of providing a method for creating a DNA construct wherein the sequence remaining after removal of the selective marker gene by site-specific recombination is not easily recognized by the R gene product, and for constructing a transformant lacking the selective marker gene by performing the transformation using the above-mentioned DNA construct.

In order to achieve the object described above, the present invention provides a DNA construct comprising an R gene under the control of an inducible promoter, and an expressible selective marker wherein the R gene and the selective marker are flanked by a pair of R sensitive sequences oriented in the same direction so as to form a removing unit which is directly or indirectly flanked by a pair of DNA fragments capable of recombination with a chromosomal DNA, wherein each of said R sensitive sequences comprises the following nucleotide sequence:

5'-<u>TTGATGAAAGAA</u> TACGTTA <u>TTCTTTCATCAA</u>-3' inverted     spacer     inverted repeat (1)  sequence  repeat (2)

or a sequence substantially identical with said nucleotide sequence, wherein the R sensitive sequence located nearest said R gene lacks 10 or less nucleotides at the end distal from the spacer sequence in the inverted repeat which is at the opposite end from the end adjacent to said R gene, and the R sensitive sequence located nearest the said selective marker gene lacks 10 or less nucleotide sequence at the end distal from the spacer sequence in the inverted repeat which is at the opposite end from the end adjacent to said selective marker gene.

BRIEF DESCRIPTION OF THE DRAWINGS

FIG. 10A is a schematic representation of the arrangement of the nucleotides sequences of R sensitive sequences when recombination occurs between a pair of R sensitive sequences. FIG. 10B is a representation of the nucleotide sequences of the resulting R sensitive sequence complex after recombination has occurred between the pair of R sensitive sequences shown in (A).

DETAILED DESCRIPTION

Figure 7:
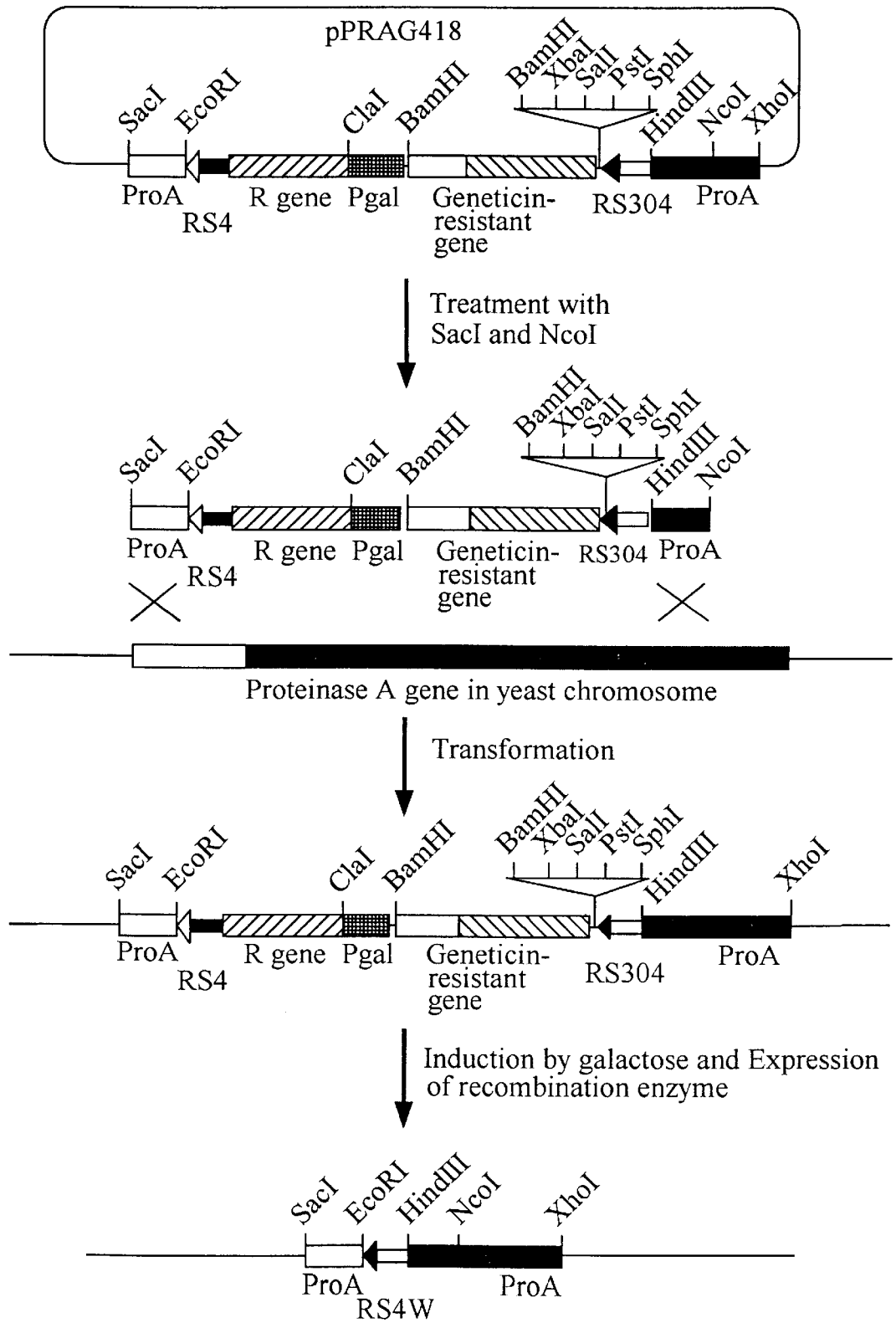
FIG. 7 shows a mechanism of destruction of the protease A gene and removal of a selective marker gene by site-specific recombination.

According to the present invention, of a pair of R sensitive sequences, an R sensitive sequence (for example RS4 in FIG. 7) located nearest the R gene (for example, the R gene in FIG. 7) lacks 10 or less nucleotides at the distant end from the spacer sequence in the inverted repeat which is at the side opposite the side adjacent to the R gene (for example, the inverted repeat (2); incidentally, the left side of RS4 in FIG. 7 is the 3'-end and the right side is the 5'-end).

Also, another R sensitive sequence (for example, RS304 in FIG. 7), which is located nearest the selective marker gene (for example, the geneticin-resistance gene in FIG. 7), lacks 10 or less nucleotides at the distant end from the spacer sequence in the inverted repeat which is at the side opposite the side adjacent to the selective marker gene (for example, the inverted repeat (1); incidentally, the left side of RS304 in FIG. 7 is the 3'-end and the right side is the 5'-end).

As an example, RS4 represented by SEQ ID No.4 lacks 6 nucleotides of the inverted repeat (2) consisting of 12 nucleotides. Also, the central 3 blocks of sequences excluding 5 nucleotides at the 5'-end and 5 nucleotides at the 3'-end (these are restriction endonuclease recognition sites, and not portions of the R sensitive sequence) of RS304-L constitute sequence RS304 in FIG. 7, and in this sequence, 6 of the 12 nucleotides constituting the inverted repeat (1) are lacking. In the R sensitive sequence of the invention, the number of nucleotides which may be lacking according to the above meaning is no more than 10, for example up to 8 and preferably only up to 6, of the nucleotides (total of 12) constituting the repeating sequence adjacent to the spacer sequence. If more than 10 nucleotides are lacking, the possibility of DNA recombination is lowered to an undesirable level.

As explained above, the R sensitive sequence of the invention includes the sequence represented by SEQ ID No.1, but with one of the inverted repeats at one side shortened as mentioned above. However the 12 nucleotides are preferably maintained at the inverted repeat at the opposite side from the shortened inverted repeat, and it may even be extended by joining 1 to 4 repeating sequences. Incidentally, as already mentioned, the naturally occurring R sensitive sequence has a structure wherein each end of the sequence represented by SEQ ID No.1 is further extended by 4 repeating sequences, and the R sensitive sequence of the present invention may also have the repeating sequence opposite from the shortened repeated sequence being repeated multiple times as in the natural sequence.

The R sensitive sequence of the present invention also encompasses those with nucleotide sequences which are substantially identical to the one defined above. Here, "substantially identical sequence" refers to a nucleotide sequence which represents a modification of the sequence defined above by substitution, deletion and/or addition of about one nucleotide in a portion other than the spacer sequence.

Figure 9:
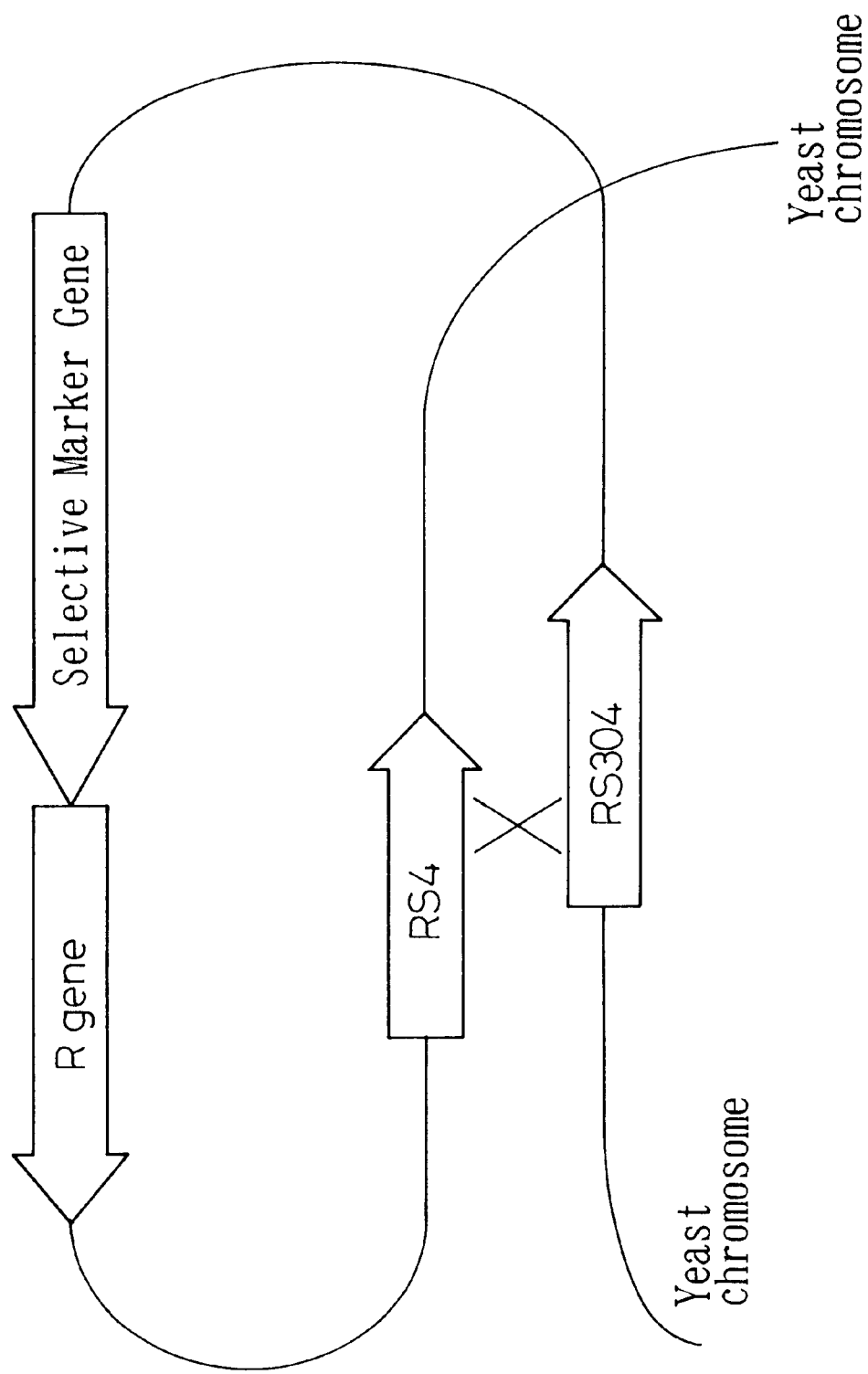
FIG. 9 shows an arrangement of a pair of R sensitive sequences when recombination occurs between the pair of R sensitive sequences. The 2 crossing lines (X symbol) indicate the site where recombination occurs.

When the R gene product acts on the DNA construct with a pair of R sensitive sequences described above, a DNA recombination results as shown, for example, in FIG. 10. That is, a pair of R sensitive sequences (for example, RS4 and RS304 in FIG. 7) are oriented as shown in FIG. 9; and as shown in FIG. 10(A), the RS4 sequence and RS304 sequence induce recombination in the overlapping region (for example, the location indicated by the 2 crossing lines in FIG. 10(A)).

As a result, as the R gene and the selective marker gene are removed, the shortened end portion of an R sensitive sequence (for example, RS4) and the shortened end portion of another R sensitive sequence (for example, RS304) are fused together and the sequence is reconstructed. The reconstructed sequence has the shortened inverted repeats at both ends of the spacer sequence, and for example, the RS4 sequence and RS304 sequence produce the RS4W sequence shown in FIG. 10(B) (SEQ ID No.5).

As will be demonstrated in Example 1, the R sensitive sequence in which inverted repeat at only one side around the spacer sequence as the center causes recombination, by the action of the R gene product; but when the inverted repeats at both sides are shortened (for example, the RS4W sequence) recombination occurs less easily by the action of the R gene product.

The inducible promoter used for expression of the R gene may be any desired inducible promoter which functions in yeast cells, and for example, a galactose-induced GAL1 promoter, a copper-induced CUP2 promoter, a heat shock-induced heat shock protein gene promoter and a low phosphate concentration-induced PHO5 promoter may be used.

The selective marker gene used may be any desired selective marker gene which can be used in yeast, and for example, the geneticin resistance gene by which a transformant can be selected in geneticin-containing medium or the cerulenin resistance gene by which a transformant can be selected in cerulenin-containing medium, may be used.

The DNA fragment which is recombinable with yeast chromosome is a DNA fragment which is homologous with a portion of a gene in the yeast chromosome, and as genes on yeast chromosomes there may be mentioned, for example, the protease A gene, ribosome DNA gene and CYC7 gene, which are genes which do not inhibit proliferation of yeast even when those genes are damaged.

The present invention also provides a method for transforming yeast using the above-mentioned DNA construct. The method comprises:

(1) introducing the above-mentioned DNA construct into yeast cells, and incorporating the DNA construct into a yeast chromosome by recombination between the yeast chromosomal DNA and DNA fragments present at both ends of the DNA construct, which are recombinable with the yeast chromosome, (2) selecting the yeast cells having the DNA construct introduced into the yeast chromosome based on expression of the expressible selective marker gene, and (3) expressing the R gene by inducing the inducible promoter, thus causing recombination between the above-mentioned pair of RS sequences, resulting in recombination both the R gene placed under the control of the inducible promoter and the expressible selection marker gene.

The transformation procedure may be repeated multiple times, and as will be explained below, this allows a plurality of target genes to be introduced into the yeast chromosome using the same selective marker.

In the method described above, the DNA construct may be introduced into yeast cells in the form of itself, a DNA fragment comprising the DNA construct or a plasmid comprising the DNA construct. The introduction may be accomplished by any known method, for example, the lithium acetate method, lithium chloride method or protoplast method.

The transformation is accomplished using a DNA construct, for example a DNA fragment, a plasmid or some other vector, comprising the R gene and the expressible selective marker gene placed between the R sensitive sequences oriented in the same direction. Since the pair of R sensitive sequences as defined above are used, the sequence remaining after recombination becomes a sequence which is not easily recognized by the R gene product, and therefore a possibility of inducing undesired recombination decreases, and the selective marker gene will be specifically removed from the transformant, and thus a desired transformant will be obtained. More specifically, by using an R sensitive sequence located nearest said R gene lacks 10 or less nucleotides at the end distal from the spacer sequence in the inverted repeat which is at the opposite end from the end adjacent to said R gene, and/or an R sensitive sequence located nearest said selective marker gene lacks 10 or less nucleotide sequence at the end distal from the spacer sequence in the inverted repeat which is at the opposite end from the end adjacent to said selective marker gene, the sequence remaining after recombination will be a sequence which is not easily recognized by the R gene product, and thus the target transformant may be obtained.

By using the method of the present invention it is possible to remove the selective marker gene without taking progeny, or additional transformation or hybridization procedures. It is also possible to omit safety evaluation of the selective marker gene. The transformants lacking the selective marker gene may also be used for subsequent transformation using the same selective marker gene, to allow repeated introduction of multiple genes.

The method of the present invention may be applied in the following manner, for introduction of, for example, a target gene A coding for a useful protein, into yeast chromosomes.

Figure 11:
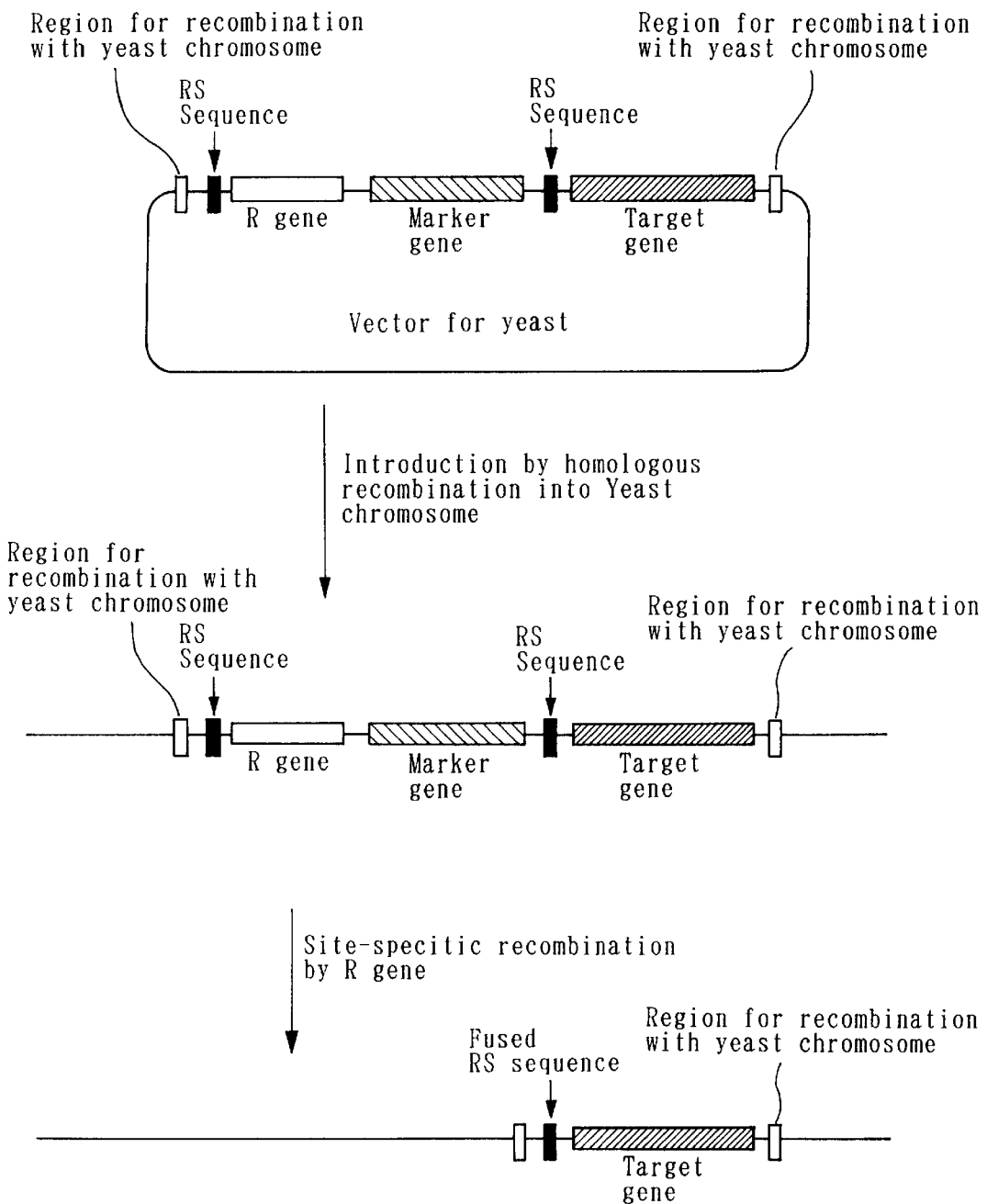
FIG. 11 is a schematic representation of a method used when a target gene is incorporated into a yeast chromosome by the method of the invention.

The DNA construct of the invention includes DNA fragments which are recombinable with yeast chromosomal DNA (sometimes to be referred to as "yeast chromosome-recombinable region") directly or indirectly linked at both ends of the DNA fragment comprising a pair of R sensitive sequences (RS sequences) oriented in the manner explained above, thus between the pair of R sensitive sequences. In the case where an R sensitive sequence is indirectly linked to a DNA fragment recombinable with the yeast chromosomal DNA, the target gene to be incorporated into the yeast chromosome is inserted between said RS sequence and said DNA fragment recombinable with the yeast chromosomal DNA (see FIG. 11).

When this DNA construct is introduced into yeast, recombination occurs between the yeast chromosome-recombinable region of the DNA construct and the corresponding chromosomal gene of the yeast, so that the DNA construct as a whole is introduced into the yeast chromosomal DNA.

The yeast may then be cultured under a condition which induces the R gene promoter so as to produce the R gene product, which acts on the R sensitive sequences (RS sequences) to cause recombination between the pair of R sensitive sequences as explained above, removing the region between the pair of R sensitive sequences (including the R gene and the marker gene), so that the target gene between the R sensitive sequences fused by recombination (with both ends shortened) and the yeast chromosome-recombinable region is left incorporated into the yeast chromosomal gene. Also, since the R sensitive sequences with both ends shortened do not induce subsequent recombination, the inserted target gene is stably maintained in the yeast chromosome.

In other words, according to the present invention the marker gene (and the R gene) is removed after the target gene has been inserted in the yeast chromosome, and the R sensitive sequences thus cease to function. Consequently, after introduction of a target gene, a gene-introducing vector containing the same marker gene (a DNA construct according to the invention) may be used for further introduction of another target gene.

EXAMPLES

The present invention will now be explained in greater detail by way of the following examples which, however, are provided only as examples and are in no way intended to restrict the scope of the invention. Unless otherwise specified, the experimental procedure was according to Sambrook et al., Molecular Cloning (Cold Spring Harbor Laboratory Press, 1989).

Example 1

Figure 1:
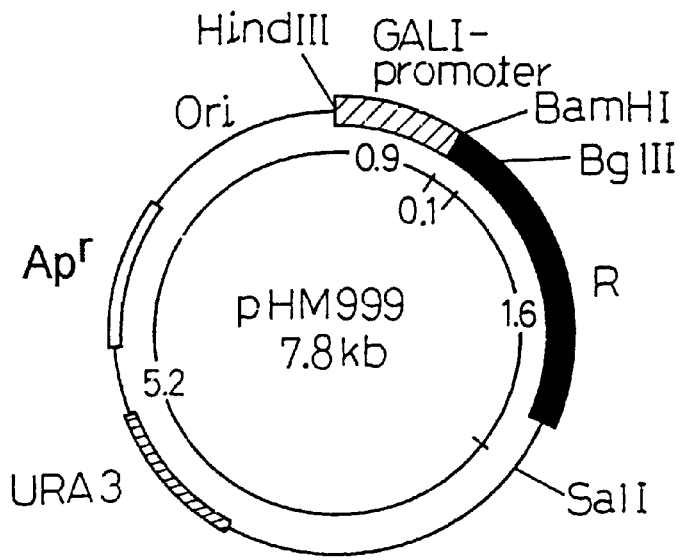
FIG. 1 shows the structure of plasmid pHM999.

Analysis of Site-Specific Recombination Enzyme-Recognizing Sequence (1) Construction of Plasmid As the R gene-expressing plasmid, a HindIII-SalI fragment containing the R gene and GAL1 promoter from pHM153 (Matsuzaki, H. et al., J. Bacteriol., 172, 610–618, 1990) was inserted between HindIII and SalI sites of the multicloning site of YEplac195 (Gietz, R. D. and Sugino, A., Gene, 74, 527–534, 1988), to construct the Ura$^+$ phenotype R protein-producing plasmid pHM999 comprising the GAL1 promoter upstream from the R gene. This plasmid is shown in FIG. 1.

Figure 2:
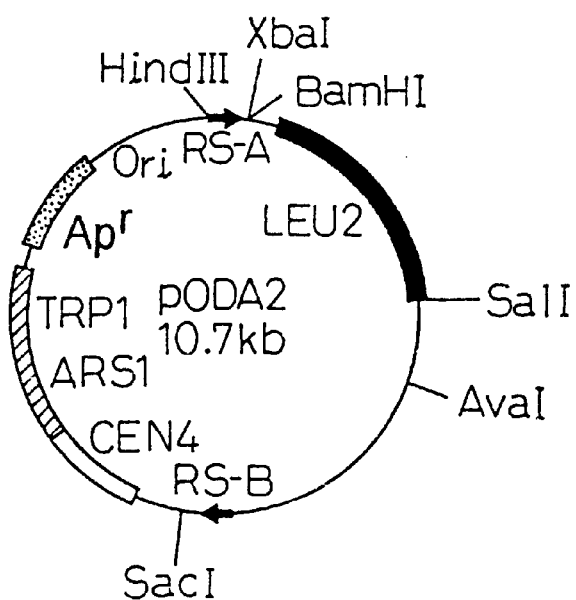
FIG. 2 shows the structure of plasmid pODA2.

Next, to prepare recombination detecting plasmid, a HindIII-BglII fragment containing the LEU2 gene of plasmid pSRT117 (Araki, H. et al., J Mol. Biol., 225, 25–37, 1992) having 2 RS sequences (designated as RS-A and RS-B, respectively) at either end of the LEU2 gene was linked to a HindIII-BamHI fragment containing the TRP1 gene of YCplac22 (Gietz, R. D. and Sugino, A., Gene, 74, 527–534, 1988) to construct the Trp$^+$Leu$^+$ phenotype plasmid pODA2. This plasmid is shown in FIG. 2.

When this plasmid undergoes recombination between the 2 RS sequences by the action of the R gene product, it is split into a 5.7 kb plasmid containing the LEU2 gene and a 4.5 kb plasmid containing the TRP1 gene. Since the plasmid containing the LEU2 gene has no selfreplicating ability in the absence of selective pressure, it is lost by the cells, causing the cells to exhibit the Leu$^-$ phenotype. In other words, recombination by the R gene product can be identified by examining the leucine requirement of the cells.

Plasmids wherein the wild-type RS from RS-A of pODA2 has been replaced with different RS sequences prepared from synthetic DNA were then constructed, utilizing the restriction enzyme sites of HindIII and XbaI or BamHI. The sequences of the synthetic DNAs used were listed below. They are various RSs wherein one inverted repeat of RS1 is increasingly shortened. They are RS1 wherein 4 repeat sequences have been deleted from the native RS sequence; various RS series wherein one inverted repeat of the RS1 is increasingly shortened; RS1M, RS2M and RS4M having point mutation which is considered to be introduced during their synthesis, as well as RS4W wherein both of the inverted repeats in the RS1 have been partially deleted.

| RS1 | TTGATGAAAGAA TACGTTA TTCTTTCATCAA | (SEQ ID No.1) |
|---|---|---|
| RS2 | TTGATGAAAGAA TACGTTA TTCTTTCATC | (SEQ ID No.2) |
| RS3 | TTGATGAAAGAA TACGTTA TTCTTCA | (SEQ ID No.3) |
| RS4 | TTGATGAAAGAA TACGTTA TTCTTT | (SEQ ID No.4) |
| RS4W | AAAGAA TACGTTA TTCTTT | (SEQ ID No.5) |
| RS5 | TTGATGAAAGAA TACGTTA TTCT | (SEQ ID No.6) |
| RS6 | TTGATGAAAGAA TACGTTA TT | (SEQ ID No.7) |
| RS7 | TTGATGAAAGAA TACGTTA | (SEQ ID No.8) |
| RS1M | TTGATGAAAGAA TACGTTA T CTTTCATCAA | (SEQ ID No.9) |
| RS2M | TTGATGAAAGAA TA GTTA TTCTTTCATC | (SEQ ID No.10) |
| RS4M | TTGATGAAATAA TACGTTA TTCTTT | (SEQ ID No.11) |

During construction of the synthetic DNAs with these sequences, there were introduced the HindIII recognition site at the 5'-end and the XbaI or BamHI recognition site at the 3'-end, and after annealing with synthesized reverse chain sequences, they were introduced between the HindIII site and the XbaI or BamHI site of pODA2. The plasmids containing RS1, RS2, RS3, RS4, RS4W, RS5, RS6, RS7, RS1M, RS2M and RS4M were designated as pODA21, pODA22, pODA23, pODA24, pODA24W, pODA25, pODA26, pODA27, pODA21M, pODA22M and pODA24M, respectively. Likewise, a plasmid was constructed with the wild-type RS from RS-B of pODA2 replaced with the following RS sequence prepared from synthetic DNA. RS201 TTGATGAAAGAA TACGTTA TTCTTCATCAA (SEQ ID No.12)

The SalI recognition site was introduced at the 5'-end and the SacI recognition site was introduced at the 3'-end during preparation of the synthetic DNA for the RS201 sequence, and after annealing with synthesized reverse chain sequence, it was used to replace the wild-type RS from RS-B of pODA2.

The plasmid with RS-A replaced with RS1 and RS-B replaced with RS201 was designated as pODA21201, and the plasmid with RS-A replaced with RS4 and RS-B replaced with RS201 was designated as pODA24201.

(2) Study of Recombination Frequency in vivo

First, strain KA311A (MAT a trp1 leu2 ura3 his3) was transformed to Ura$^+$ phenotype with pHM999, and the resulting transformant was transformed with pODA2 which contains the 225 bp wild-type recombination site and a Ura$^+$ Trp$^+$ Leu$^+$ strain was selected. The strain was cultured at 30° C. overnight in 50 g/L galactose or glucose liquid medium with Ura$^-$Trp$^-$ selective pressure, and the R gene on pHM999 was expressed to induce recombination between the 2 RS sequences on pODA2.

The culture solution was diluted and applied onto Ura$^-$Trp$^-$ selective medium, and then static cultured at 28° C. for 2 days. This was replicated on Leu$^-$ selective medium and the colonies were counted. The cells which proliferated in Ura$^-$Trp$^-$ did not proliferate in Leu$^-$ selective medium were the cells in which recombination had occurred.

In the same manner, the different plasmids prepared in Example 1 (1) were also introduced into strains carrying pHM999, and the recombination frequency in galactose and glucose medium was investigated.

The results are listed in Table 1.

TABLE 1

| | R sensitive to sequence site | | Recombination frequency (in vivo; %) | | (in vitro) |
|---|---|---|---|---|---|
| Plasmid | A | B | Gal | Glu | |
| pODA2 | wild-type RS | wild-type RS | 100 | 26 | ++ |
| pODA21 | RS1 | wild-type RS | 100 | 14 | ++ |
| pODA22 | RS2 | wild-type RS | 100 | 12 | ++ |
| pODA23 | RS3 | wild-type RS | 100 | 0 | + |
| pODA24 | RS4 | wild-type RS | 98 | 0 | + |
| pODA24W | RS4W | wild-type RS | 37 | 0 | – |
| pODA25 | RS5 | wild-type RS | 17 | 0 | – |
| pODA26 | RS6 | wild-type RS | 2 | 0 | – |
| pODA27 | RS7 | wild-type RS | 0 | 0 | – |
| pODA21M | RS1M | wild-type RS | 3 | 0 | – |
| pODA22M | RS2M | wild-type RS | 4 | 0 | – |
| pODA24M | RS4M | wild-type RS | 48 | 0 | – |
| pODA21201 | RS1 | RS201 | 100 | 84 | ++ |
| pODA24201 | RS4 | RS201 | 99 | 5 | – |

++ = high recombination frequency
+ = slight recombination
+– = recombination with increased R protein amount
– = no recombination As shown in Table 1, 100% recombination efficiency occurred in galactose medium with pODA2. Also, 26% recombination efficiency occurred in the glucose medium.

Furthermore, no difference in recombination frequency was seen between the strains with pODA2 and the strains with pODA21 in either the galactose medium or the glucose medium. Consequently, it is thought that the 4 repeating sequences are not necessary at least for recombination.

Also, while roughly 100% frequency of recombination occurred with pODA21, pODA22, pODA23 and pODA24 in the galactose medium, the frequency fell sharply with pODA25, and virtually no recombination occurred with pODA26 and pODA27. In the glucose medium, pODA21 and pODA22 had about the same recombination frequency as pODA2. This demonstrated that one of the inverted repeats should preferably have at least 2 bp for recombination.

On the other hand, virtually no recombination occurred on pODA22M which was a plasmid with a point mutation on RS and a mutation on the spacer portion, or on pODA21 which had a mutation near the spacer portion, while 48% recombination frequency occurred in galactose medium with pODA24M. Thus it may be concluded that for efficient recombination it is essential for the spacer portion to be conserved.

With the strain carrying pODA24W, 37% recombination frequency occurred in galactose medium, and thus a large difference was seen in the recombination frequencies of the strains carrying pODA24. This indicates that lack of both repeating sequences results in vastly lower recombination ability than lack of only one.

(3) Study of Recombination Frequency in vitro

Partially purified recombinant R protein produced by transformed *E. coli* was used to determine the recombination frequency with mutant RS-carrying plasmids in vitro. The measurement of the in vitro recombination efficiency was made according to the following method. The DNA and 1 μl of partially purified recombinant R protein produced by transformed *E. coli* (Biorex70 fraction: Araki, H et al., J. Mol. Biol., 225, 25–37, 1992) were added to 100 μl of a reaction solution comprising 50 mM Tris-HCl (pH 7.4) and 10 mM MgCl$_2$, and reaction was conducted at 30° C. for 30 minutes. After ethanol precipitation, an appropriate restriction endonuclease was used for cutting and confirmation was made by agarose electrophoresis. The results are listed in Table 1 above.

pODA2, pODA21, pODA22 and pODA21201 had a high recombination frequency, and slight recombination was detected with pODA23. With pODA24, recombination was detected when the amount of R protein was increased by 2- to 6-fold. No recombination was detected with pODA24W, pODA25, pODA26, pODA27, pODA21M, pODA22M, pODA24M and pODA24201.

Example 2

Destruction of Yeast Protease A Gene (1) Construction of R Sensitive Sequence-Containing Plasmid pRS304-4

Four different oligonucleotides were synthesized for introduction of the R sensitive sequence into plasmids.

(RS4-S) 5'-C TTGATGAAAGAA TACGTTA TTCTTT G-3' (SEQ ID No.13)

(RS4-L) 5'-AATTC AAAGAA TAACGTATTCTTTCAT-CAA GAGCT-3' (SEQ ID No.14)

(RS304-S) 5'-C TTGATGAAAGAA TAACGTA TTCTTT A-3' (SEQ ID No.15)

(RS304-L) 5'-AGCTT AAAGAA TACGTTA TTCTTTCATCAA GCATG-3' (SEQ ID No.16)

Figure 3:
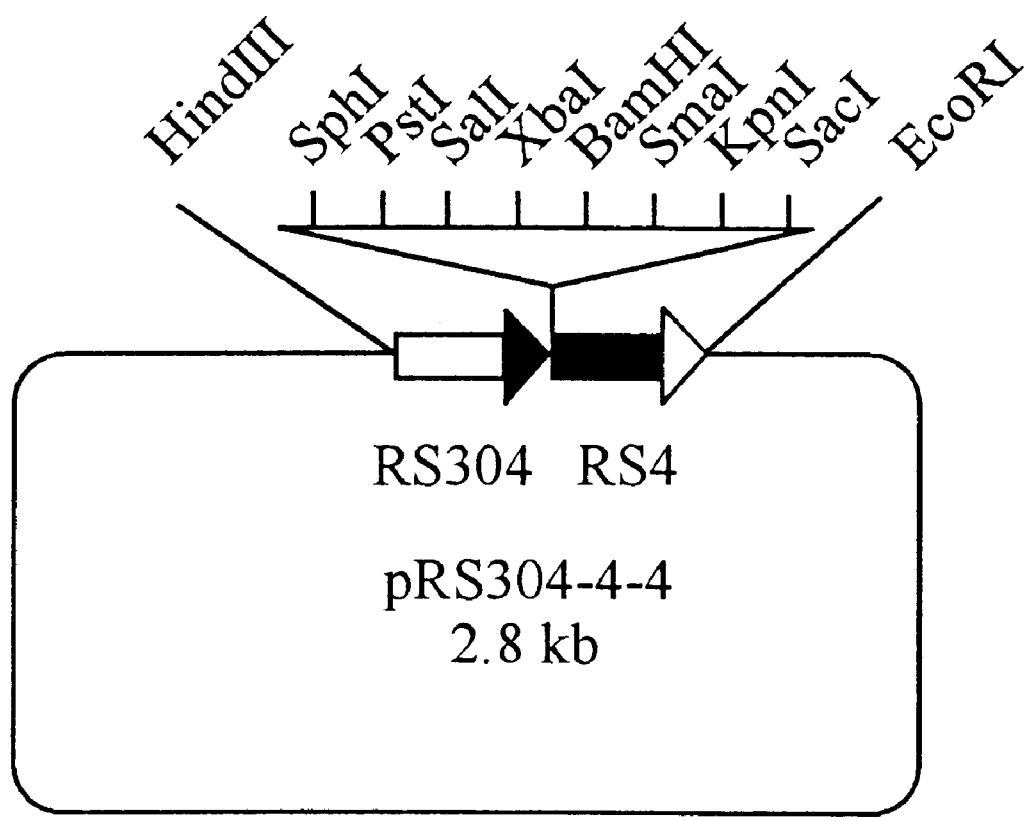
FIG. 3 shows the structure of plasmid pRS304-4-4.

First, the commercially available plasmid pUC19 was cleaved with restriction endonucleases EcoRI and SacI. The synthetic DNA sequences RS4-S and RS4-L were annealed, and ligated with the EcoRI-SacI fragment of pUC19 to construct pRS4. pRS4 was then cleaved with restriction endonucleases SphI and HindIII and ligated with the synthetic DNA sequences RS304-S and RS304-L to construct plasmid pRS304-4-4. This is shown in FIG. 3.

(2) Construction of Plasmid for Transformation (2-1) Preparation of Plasmid pRS153dB1

In plasmid pHM153 for expression of the R gene, the R gene is expressed under the control of a promoter (GAL1 promoter) which induces its expression in galactose. After digesting pHM153 with BamHI, a DNA Blunting Kit (product of Takara Shuzo) was used for blunting of the ends.

Figure 4:
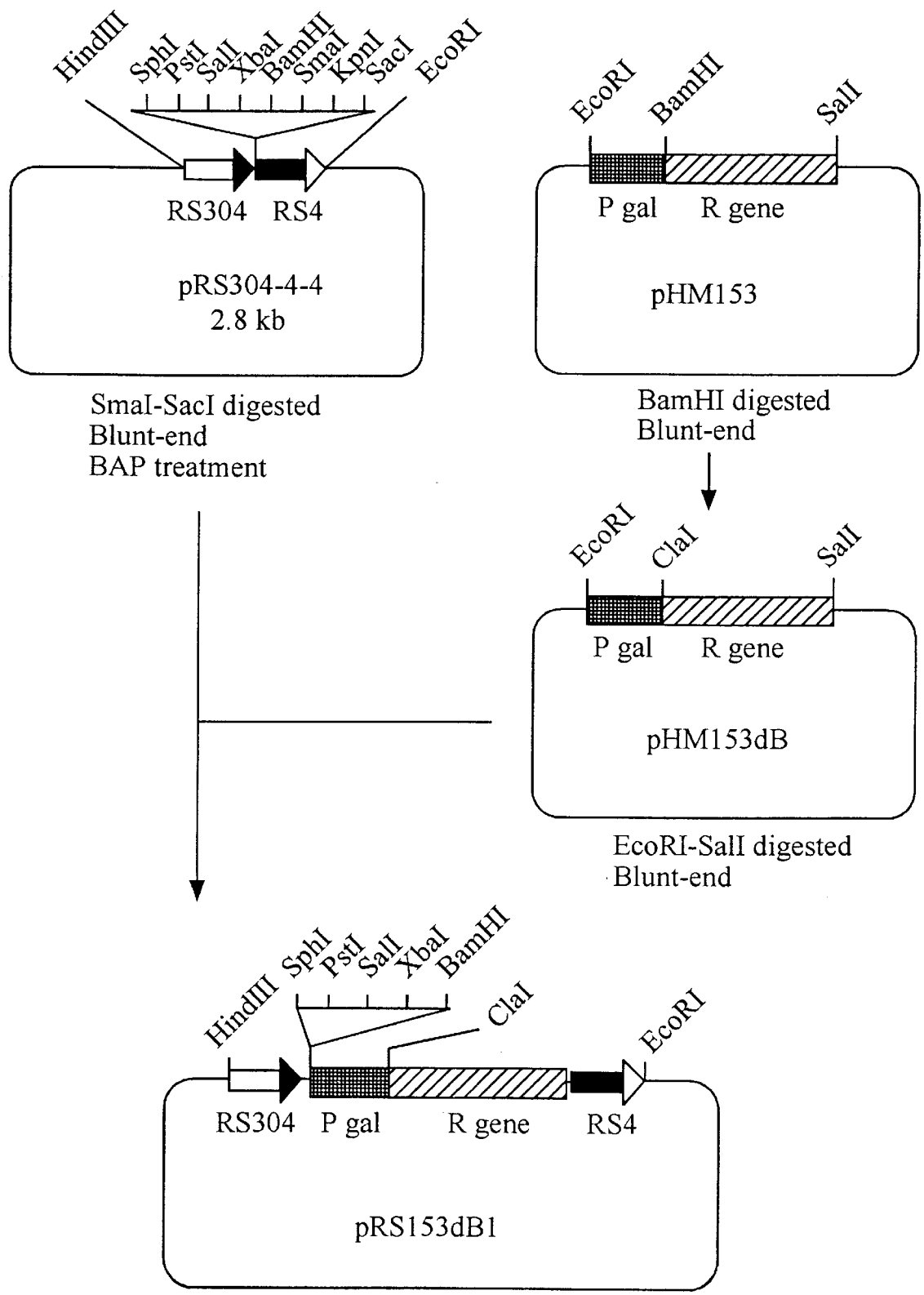
FIG. 4 shows a process for the construction of plasmid pRS153dB1.

The plasmid obtained by self-ligation of the resulting DNA fragments was designated as pHM153dB. Digestion of plasmid pRS304-4-4 obtained in Example 2 (1) with SmaI and SacI was followed by blunting of the ends in the same manner. An approximately 2.8 kb DNA fragment obtained by treating pHM153dB with EcoRI and SalI and then blunting the end was incorporated into the previously obtained approximately 2.9 kb DNA fragment, and the resulting plasmid was designated as pRS153dB1. This is shown in FIG. 4.

(2-2) Preparation of Plasmid pPRA153dB1

Figure 5:
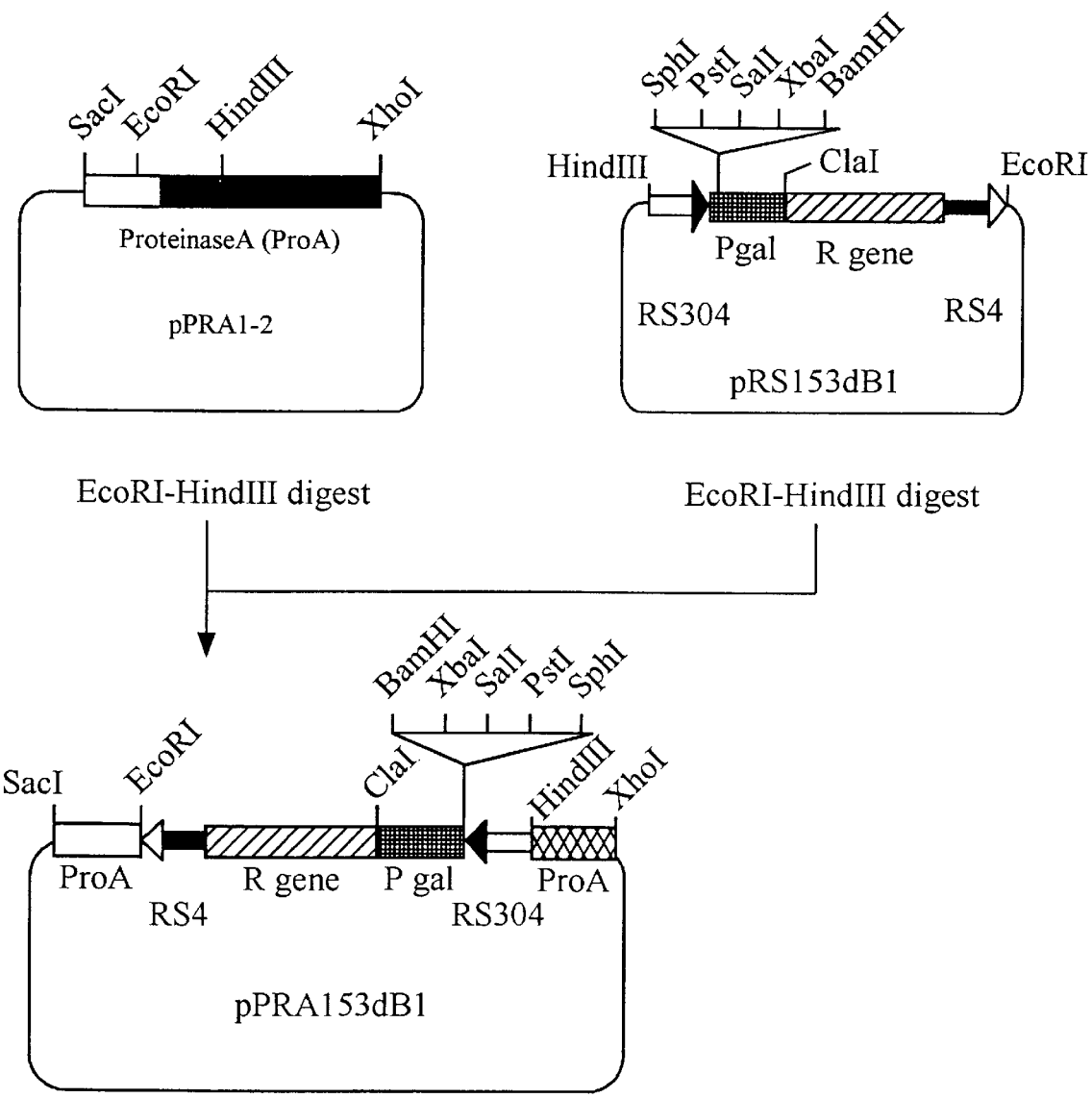
FIG. 5 shows a process for the construction of plasmid pPRA153dB1.

An approximately 2.8 kb DNA fragment obtained by digesting plasmid pRS153dB1 with EcoRI and HindIII was linked with an approximately 4.2 kb DNA fragment obtained by digesting plasmid pPRA1-2 (Woodford, C. A. et al., Mol. Cell. Biol., 6, 2500–2510, 1988) containing the total length of the yeast (*Saccharomyces cerevisiae*) protease A gene with EcoRI and HindIII, and the resulting plasmid was designated as pPRA153dB1. This is shown in FIG. 5. The approximately 4.2 kb DNA fragment obtained by digesting plasmid pPRA1-2 with EcoRI and HindIII lacks 136 N-terminal amino acid residues which include the initiation codon ATG, and 82 bp of the 5' upstream region of protease A.

(2-3) Preparation of Plasmid pPRAG418

Figure 6:
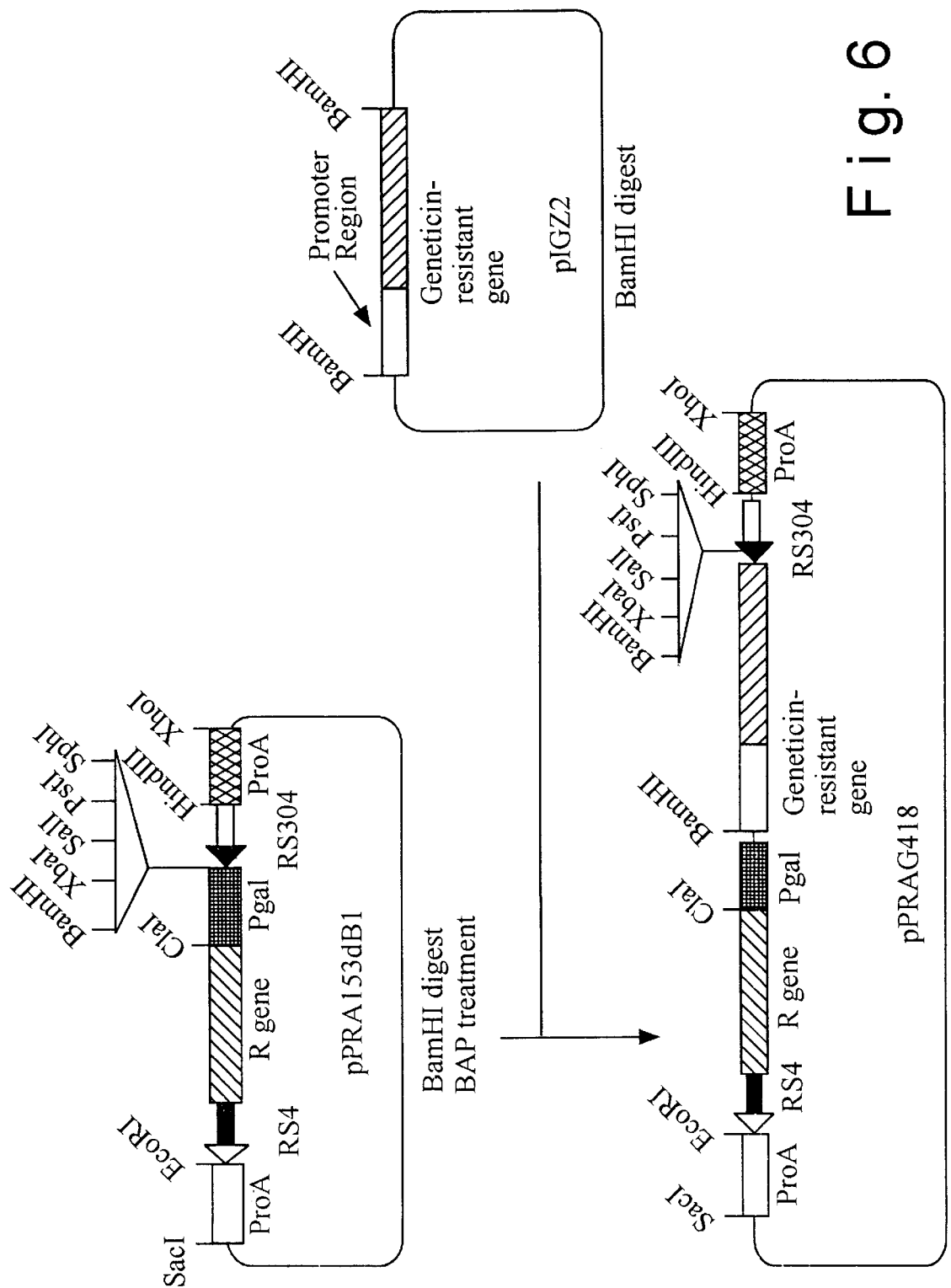
FIG. 6 shows a process for the construction of plasmid pPRAG418.

A DNA fragment obtained by digestion of plasmid pPRA153dB1 with BamHI followed by dephosphorylation with *E. coli* (*E. coli* A19) alkaline phosphatase was linked with an approximately 2.4 kb DNA fragment obtained by digesting plasmid pIGZ2 (Nakazawa, N. et al., J. Ferment. Bioeng., 73, 265–270, 1992) with BamHI, to prepare plasmid pPRAG418. This is shown in FIG. 6. The BamHI fragment contains the gene conferring G418 resistance linked downstream from the glyceraldehyde 3-phosphate dehydrogenase gene promoter which is one of the constitutive promoters of yeast.

(3) Removal of Marker Gene Using Laboratory Strain

R27-7C-1C (MAT α trp1 leu2 his3 ura3) was used as the haploid yeast. The transformation of the yeast can be accomplished by a method using lithium chloride (Kodama, Y. et al., J. Am. Soc. Brew. Chem., 53, 24–29, 1995). An approximately 5.8 kb DNA fragment (approximately 10 μg) obtained by treating pPRAG418 obtained in Example 2 (2-3) with SacI and NcoI was used for recombination in yeast, and the transformants were selected based on geneticin resistance. That is, yeast cells transformed by the aforementioned procedure were plated onto a YPD agar plate (2% peptone, 2% glucose, 1% yeast extract, 2% agar) containing a 300 μg/ml concentration of geneticin, and were incubated at 30° C. for 72 hours.

Since only the transformants carrying the G418 gene can grow in this agar medium, the appearing colonies were selected as the transformants. Upon culturing of the obtained transformants in medium containing galactose, the gene coding for the R protein was expressed so that production of the R protein was induced in the yeast cells. The produced R protein recognizes the recognition sequences inserted at both ends of the G418 drug resistance gene, and thus the region between the recognition sequences can be cut out and removed. Here, the resulting transformant colonies were cultured at 30° C. for 48 hours in 10 ml of YPGal (2% peptone, 5% galactose, 1% yeast extract) liquid medium to induce recombination between the recognition sequences.

After diluting the culture medium 100,000-fold with sterilized water, 20 μl thereof was plated onto YPD agar medium and cultured at 30° C. for 48 hours. Of the approximately 10,000 colonies which resulted, 11 strains were selected at random and cultured at 30° C. for 48 hours each in YPD agar medium containing a 600 μg/ml concentration of geneticin and the same medium without geneticin. All of the selected 11 strains were able to grow only in the medium without geneticin, indicating that the selective marker gene had been removed.

FIG. 7 shows an illustrative summary of the destruction of the protease A gene and removal of the selective marker by the site-specific recombination described above.

(4) Removal of Marker Gene Using Brewer's Yeast (4-1) First Transformation

Production of the transformants was accomplished by the same method as used for the laboratory strain. The high polyploid brewer's yeast strain BH84 (Kodama, Y. et al., J. Am. Soc. Brew. Chem., 53, 24–29, 1995) was used as the host, but any yeast which is at least diploid may be used. The colonies of the resulting transformants were cultured at 30° C. for 48 hours in 10 ml of YNB liquid medium containing 5% galactose.

Culturing in the galactose-containing medium resulted in expression of the gene coding for the R protein and production of the R protein in the yeast cells. The R protein recognizes the recognition sequences inserted at both ends of the G418 drug resistance gene, and thus this R sensitive sequence portion can be cut out and removed. Consequently, the culture solution after 48 hours of culturing in yeast minimal medium (Yeast Nitrogen Base w/o amino acid) liquid medium containing 5% galactose was diluted 100,000-fold with purified water, and 20 μl thereof was looped onto YNB agar medium containing 5% galactose and cultured at 30° C. for 48 hours.

Of the approximately 10,000 colonies which resulted, 125 strains were selected and cultured at 30° C. for 48 hours each in yeast minimal agar medium containing 2% glucose and 600 μg/ml of geneticin and the same medium containing no geneticin. One strain was obtained which could not grow in the medium containing geneticin but could grow in the medium without geneticin.

(4-2) Second Transformation

The protease A gene obtained by the procedure described above was destroyed once and a second transformation was carried out based on a strain lacking the resistance marker. The preparation of the competent cells and transformation using plasmid pPRAG418 were both accomplished under the same conditions as the first transformation. Upon selection of the transformants with the same geneticin-containing YPD agar medium used for the first transformation, 5 geneticin-resistant transformants were obtained.

One of the 5 transformants obtained by the procedure described above was selected, and the selective marker gene was cut out and removed. Induction of the R protein and removal of the selective marker gene were carried out in the same manner as the first time. As a result, 3 strains were obtained which could not grow in the medium containing 600 μg/ml geneticin but could grow in medium without no geneticin.

(4-3) Destruction of Protease A Gene

Success of the transformation and destruction of the chromosomal gene coding for protease A can be confirmed by Southern blotting analysis in the following manner. The chromosomal DNA of the transformants after expression of the R gene was extracted by a common method, and cut with restriction endonuclease HindIII. Electrophoresis in an agarose gel was followed by blotting in nitrocellulose, and a 1.9 kbp fragment isolated from the plasmid coding for protease A (pPRA1-2) with restriction endonuclease SacI and XhoI was used as a probe for Southern blotting.

Figure 8:
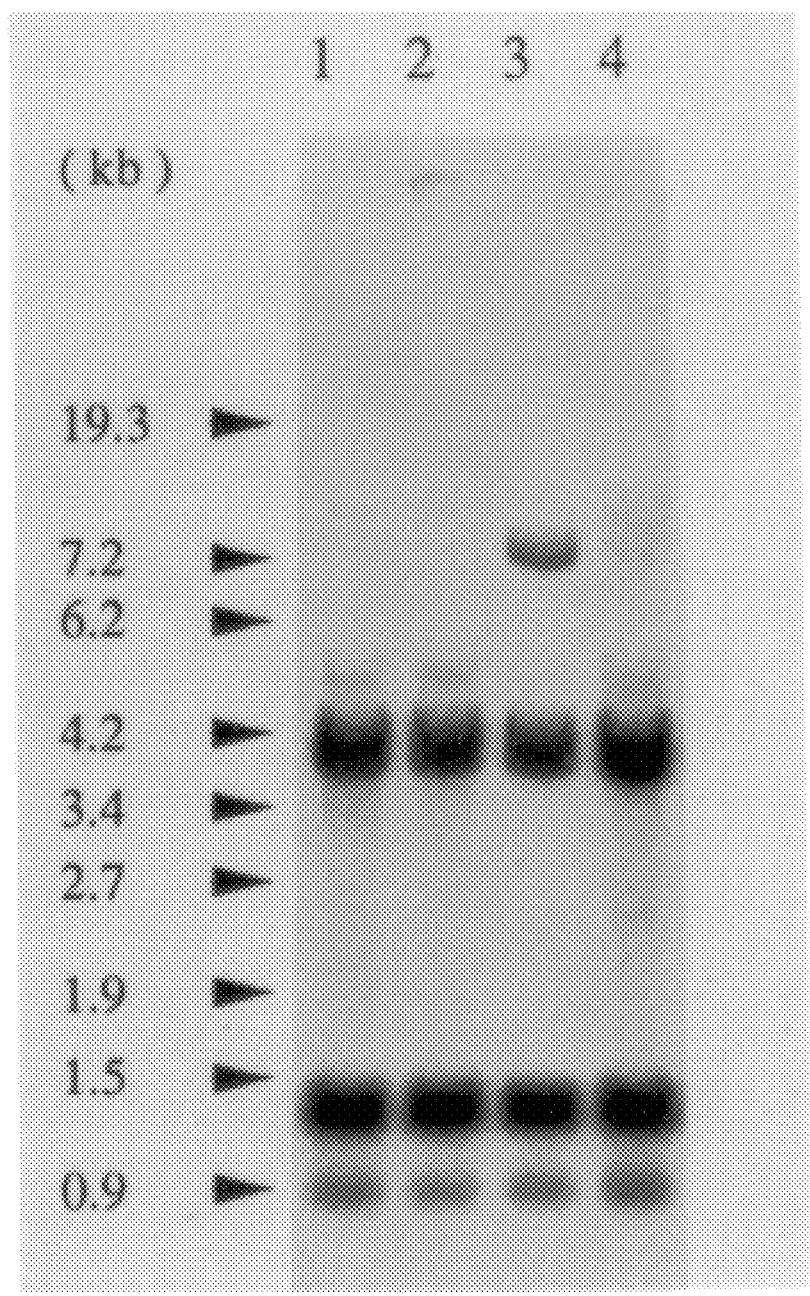
FIG. 8 shows the results of Southern blotting analysis.

As a result, 4.2 and 1.2 kb bands were detected in the wild strain (lanes 1 and 2 in FIG. 8), 7.9 and 1.2 kb bands were detected in the first transformation (lane 3 in FIG. 8), and 3.7 and 1.2 kb bands were detected in the transformants after expression of the R gene (lane 4 in FIG. 8). The number of gene-destroyed chromosomes can be estimated from the darkness of the bands. Thus, there were identified a strain with one gene destruction and a strain with 2 genes destructions of the protease A gene. The results are shown in FIG. 8.

Example 3

Introduction of Rhizopus-Derived Glucoamylase Gene into Wild Yeast

The yeast (*Saccharomyces cerevisiae*) strain AY-01 is diploid. By repeating the transformation and the removing of the marker gene in the specific recombination sequence twice during introduction of the glucoamylase gene, it is possible to introduce only the glucoamylase gene at both of the opposite corresponding positions of the chromosome.

1. Construction of Plasmid pUPRGA3 for Transformation

Four different oligonucleotides were synthesized for introduction of the R sensitive sequences into plasmids.

(RS3-S) 5'-C TTGATGAAAGAA TACGTTA TTCTTTCA-3' (SEQ ID No: 17)
(RS3-L) 5'-AATTC TGAAAGAA TAACGTA TTCTTTCATCAA GAGCT-3' (SEQ ID NO: 18)
(RS303-S) 5'-C TTGATGAAAGAA TAACGTA TTCTTTCA-3' (SEQ ID NO: 19)
(RS303-L) 5'-AGCT TGAAAGAA TACGTTA TTCTTTCATCAA GCATG-3' (SEQ ID NO: 20)

After phosphorylation of the 5'-ends of these synthesized DNA sequences, and annealing of RS3-S with RS3-L, and RS303-S with RS303-L, the former was inserted into the restriction endonuclease EcoRI-SacI sites of pUC19, and then the latter was inserted into the restriction endonuclease SphI-HindIII sites, to construct plasmid pRS303-3.

Figure 12:
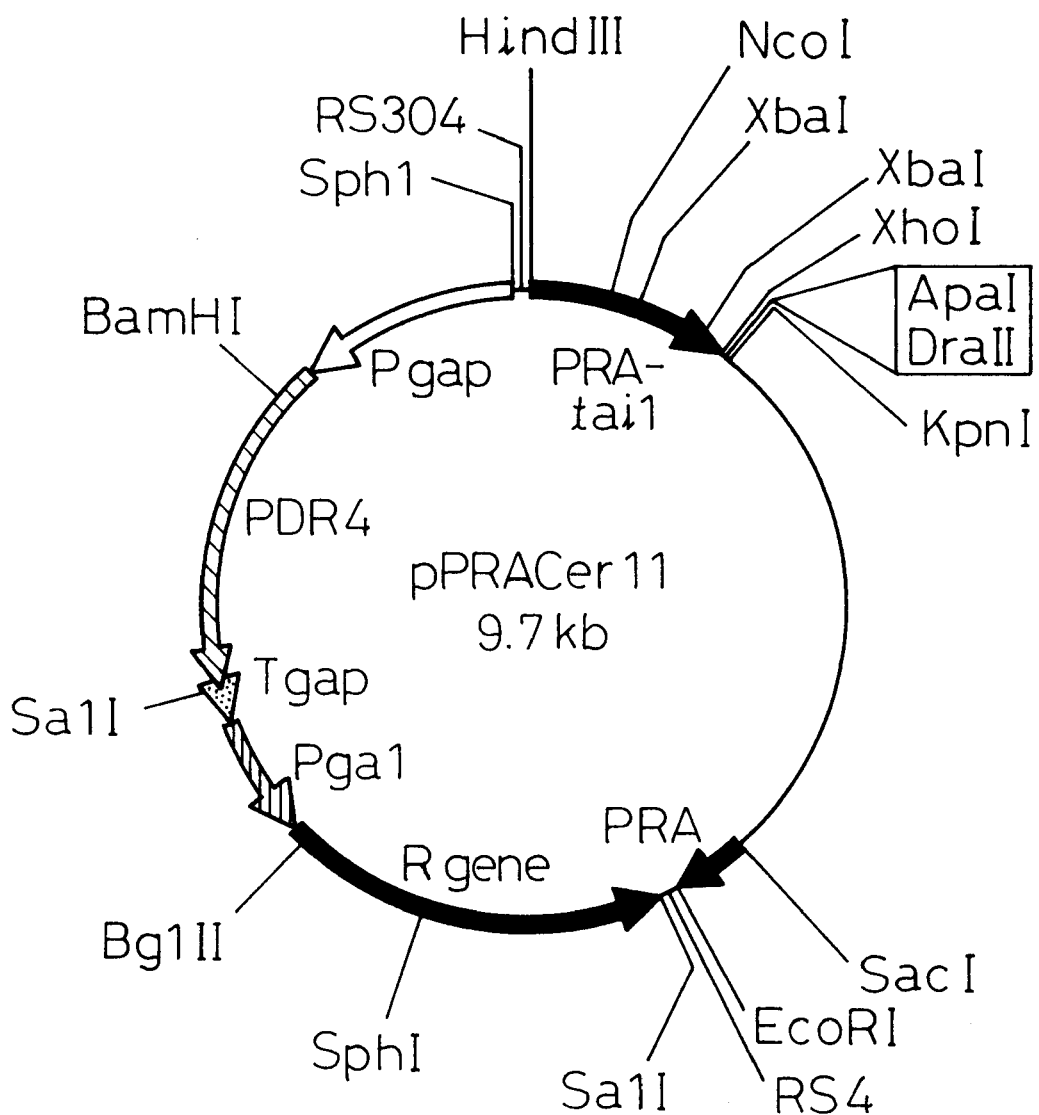
FIG. 12 shows the structure of plasmid pPRACer11.

A 2.7 kb fragment obtained by digestion of pRS303-3 with restriction endonuclease SacI, blunting of the ends with a Blunting Kit (product of Takara Shuzo) and then digestion with restriction endonuclease SphI, was linked with a 2.7 kb fragment obtained by digestion of plasmid pPRACer11 (FIG. 12) with restriction endonuclease SalI, blunting of the ends with a Blunting Kit and digestion with restriction endonuclease SphI, to obtain plasmid pRS303-3-Cer.

The 2.7 kb fragment obtained by digesting pPRACer11 with restriction endonuclease SalI was inserted at the restriction endonuclease SalI site of pRS303-3-Cer to construct plasmid pRCer303-3-1.

After digestion of pRCer303-3-1 with HindIII the ends were blunted with a Blunting Kit and a pSmaI linker (product of Takara Shuzo) was introduced to construct pRCer303-3-2.

Plasmid pUC19 was digested with restriction endonuclease EcoRI and HindIII, and a 5.5 kb fragment obtained by digesting pRCer303-3-2 with restriction endonuclease SmaI and EcoRI was linked with a 1.1 kb restriction endonuclease HindIII and SmaI fragment containing the URA3 gene of YEp24 (Botstein, D. et al., Gene, 8, 17, 1979) and inserted therein to construct pU5'RCerRS3.

Plasmid pUC18 was digested with restriction endonucleases EcoRI and SphI, and after blunting of the ends with a Blunting Kit (Takara Shuzo), was linked to construct pUC18HSp. A 1.2 kb restriction endonuclease HindIII fragment containing the URA3 gene of YEp24 was inserted at the restriction endonuclease HindIII site thereof to construct pURA34.

A pEcoRI linker (Takara Shuzo) was inserted at the SmaI site of pURA34 to construct pURA35, and after digestion thereof with restriction endonuclease EcoRI, a 2.8 kb fragment from partial digestion with restriction endonuclease HindIII was linked with a 6.6 kb restriction endonuclease HindIII-EcoRI fragment of pU5'RCerRS3 to construct plasmid pUPRRS3.

A 3.2 kb restriction endonuclease HindIII fragment of PYGA2269 (Ashikari, T. et al., Appl. Microbiol. Biotechnol., 30, 535, 1989) was inserted at the restriction endonuclease SmaI site of pUPRRS3 after blunting of the ends with a Blunting Kit (Takara Shuzo), to construct plasmid pUPRGA3 (FIG. 13).

Figure 13:
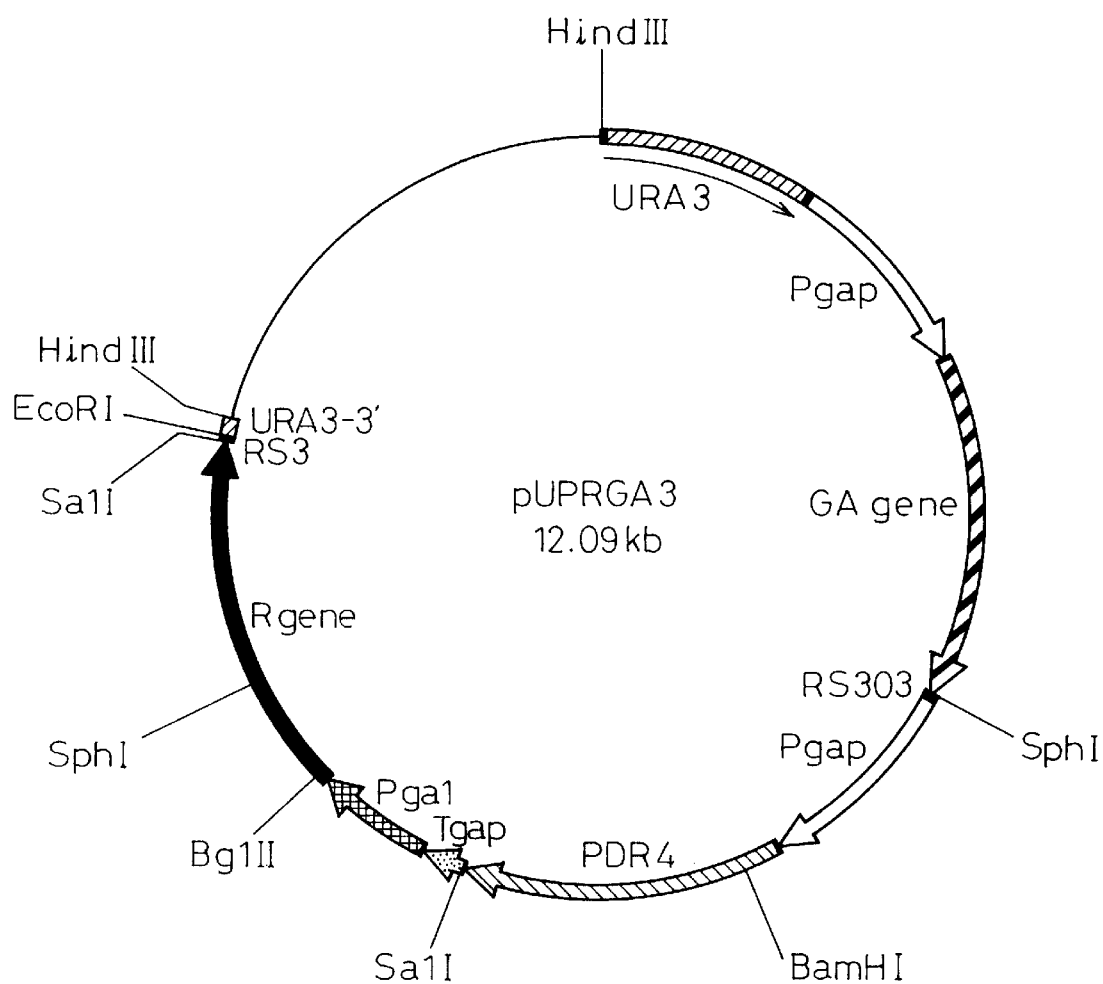
FIG. 13 shows the structure of plasmid pUPRGA3.

As FIG. 13 shows, this plasmid includes the following genes inserted downstream from the coding region of the URA3 gene.

A. A constitutively expressed glucoamylase gene linked to the yeast glyceraldehyde 3-phosphate dehydrogenase (GAP) promoter. This is the gene whose introduction is the object of this example.

B. A marker gene (PDR4; cerulenin and cycloheximide resistance gene) and the R gene for an enzyme which catalyzes recombination between site-specific recombination sequences, which are both flanked by those site-specific recombination sequences (RS303, RS3). The R gene is linked to the GAL1 promoter so that its expression is induced by galactose. These genes were designed so as to be removed by recombination with the site-specific recombination sequences after selection of the transformants.

2. Transformation (1)

For the transformation, 5 μg of plasmid pUPRGA3 was digested with restriction endonuclease HindIII and the total amount was used after ethanol precipitation and dissolution in 10 μl of TE buffer solution. The yeast (*Saccharomyces cerevisiae*) strain AY-01 (a/α wild-type) was used as the host for transformation by the lithium method with a restriction endonuclease HindIII digestion product of plasmid pUPRGA3. After spreading out on a YPD plate containing 1.0% cycloheximide and culturing at 30° C. for 3 days, the cycloheximide-resistant strains were selected.

Of the approximately 400 transformant strains which resulted, 4 strains (GA3-PDR4-#1, #2, #3, #4) were analyzed by Southern blotting. The chromosomes were digested with restriction endonuclease HindIII and the URA3 gene was probed. As a result, 1.2 kb and 9.7 kb fragments were detected in all 4 strains. In comparison with the parent strain AY-01, this indicated insertion of 8.5 kb at one of the URA3 gene positions of the chromosome, and thus it was concluded that both A and B above had been inserted.

3. Removing of Marker Gene (1)

For removing of the marker gene, one loopful of the transformants obtained in Example 3-2 (GA3-PDR4-#1, #2, #3, #4) was transferred into 10 ml of synthetic medium (6.7 g yeast nitrogen base w/o amino acid, 2g/1L galactose) and shake cultured at 30° C. overnight to induce the R gene. After appropriate dilution they were spread out on a YPD plate and cultured for 3 days at 30° C. From the colonies from each transformant, 200 were selected for a total of 800 strains, and after replication on a YPD plate and a YPD plate containing 1.0 mg/ml cycloheximide, they were cultured at 30° C. for 3 days and the cycloheximide resistance was determined. As a result, 3 cycloheximide-sensitive strains were obtained (GA3-#1028, #1151, #1171). Upon analyzing these strains by Southern blotting, 4.2 kb and 1.2 kb fragments were detected in the 3 strains GA3-#1028, #1151 and #1171, indicating that about 3 kb had been inserted in the URA3 region of one of the chromosomes. This indicates that the markers are removed from the transformants by site-specific recombination, and that only the glucoamylase gene remained inserted.

4. Transformation (2)

GA3-#1028 and #1171 were transformed in the same manner as in Example 3-2. The transformants obtained were 6 from the former and 3 from the latter. These were analyzed by Southern blotting. As a result, 4.2 kb and 9.7 kb fragments were detected in one strain (GA3-PDR4-#135). This indicates that only A had been inserted at the URA3 gene position of one chromosome, while A and B had both been inserted at the other, and it was concluded that a new gene had been inserted on a different chromosome than the one which already had the gene inserted.

5. Removing of Marker Gene (2)

Strain GA3-PDR4-#135 was cultured for 2 days in galactose-containing medium as in Example 3-3 to induce the R gene. The cycloheximide resistance of 400 strains were selected and examined for cycloheximide resistance. As a result, 7 strains (GA3-#5197, #5198, #5199, #5200, #6198, #6199, #6200) exhibited cycloheximide-sensitive. These strains formed slightly larger colonies on their YPD plates after induction. Upon analysis by Southern blotting a 4.2 kb fragment was detected, indicating an insertion of approximately 3 kb in the URA3 region of both chromosomes, and it was concluded that only the glucoamylase gene had been inserted.

6. Expression of Glucoamylase Gene

One loopful each of the parent strain AY-01 and 3 glucoamylase gene-introduced strains (GA3-PDR4-#1, GA3-#1028, GA3-#5197) were transferred to YPD medium and cultured at 30° C. for 18 hours. A portion of the culture solution was taken and measured for glucoamylase activity using the supernatant after centrifugal separation. The measurement was made using soluble starch which had been gelatinized by heating, and assaying the amount of liberated glucose after reaction at 40° C. One unit of glucoamylase enzyme activity was defined as the activity which liberated 1 μmole of glucose at 40° C. in one minute. As a result, absolutely no glucoamylase activity was exhibited in the parent strain AY-01, but the 3 glucoamylase gene-introduced strains GA3-PDR4-#1, GA3-#1028 and GA3-#5197 each respectively secreted 0.173, 0.179 and 0.389 units of glucoamylase per milliliter of culture supernatant.

[Effect of the Invention]

A technique for removing selective markers from transformants has thus been established using a site-specific recombination mechanism in yeast. As a result, it has become possible to remove selective marker genes from transformants without subsequent transformation or hybridization procedures. In addition, by using the pair of R sensitive sequences as defined according to the invention, the sequence remaining after recombination becomes a sequence which is no longer easily recognized by the R protein, and therefore after removal of the selective marker gene, the transformant may be used again for transformation using the same selective marker.

This means that the technique allows the same selective marker to be theoretically used for introduction of an unlimited number of genes into the same cell. Moreover, since this method of the present inventors may be used to specifically remove selective marker genes from transformants, it is possible to eliminate consideration of the selective marker gene in evaluating the safety of the recombinant, and thus a very useful technique is provided for the industrial use of bred individuals.

We claim:

1. A DNA construct comprising an R gene positioned under the control of an inducible promoter, and an expressible selective marker wherein the R gene and the selective marker are flanked by a pair of R sensitive sequences oriented in the same direction so as to form a removing unit which is directly or indirectly flanked by a pair of DNA fragments capable of recombination with a chromosomal DNA, wherein each of said R sensitive sequences comprises the following nucleotide sequence:

```
5'-TTGATGAAAGAA TACGTTA TTCTTTCATCAA-3' inverted        spacer      inverted repeat (1)      sequence    repeat (2)
``` or a sequence substantially identical with said nucleotide sequence,
   wherein the R sensitive sequence located nearest said R gene lacks between 1 and 10 nucleotides at the end distal from the spacer sequence in the inverted repeat which is at the opposite end from the end adjacent to said R gene, and the R sensitive sequence located nearest said selective marker gene lacks between 1 and 10 nucleotides at the end distal from the spacer sequence in the inverted repeat which in at the opposite end from the end adjacent to said selective marker gene.

2. A DNA construct according to claim 1, wherein a target gene to be incorporated into a chromosome of yeast is inserted between a DNA fragment which is recombinable in the chromosomal DNA of said yeast and the R sensitive sequence near it.

3. A plasmid comprising the DNA construct according to claim 1.

4. A method for transforming yeast, comprising the steps of:

(1) introducing a DNA construct according to claim 1 into yeast cells, and incorporating said DNA construct into a yeast chromosome by recombination between the yeast chromosomal DNA and DNA fragments present at both ends of said DNA construct, which are recombinable with the yeast chromosome;

(2) selecting the yeast cells having said DNA construct introduced in the yeast chromosome based on expression of said expressible selective marker gene; and (3) expressing the R gene by inducing said inducible promoter, thus causing recombination between said pair of R sensitive sequences, resulting in removing both the R gene placed under the control of said inducible promoter and the expressible selection marker gene.

5. A method according to claim 4, wherein the DNA construct comprises a target gene to be incorporated into the yeast chromosome inserted between a DNA sequence recombinable with said yeast chromosomal DNA and the R sensitive sequence near it.

6. A method according to claim 4, wherein said steps are releated.

7. A method according to claim 6, wherein said steps are repeated more than once.

8. A plasmid comprising the DNA construct according to claim 2.

9. A method according to claim 5, wherein said steps are repeated.

10. A method according to claim 9, wherein said steps are repeated more than once.

* * * * *

UNITED STATES PATENT AND TRADEMARK OFFICE
CERTIFICATE OF CORRECTION

PATENT NO. : 5,965,444 Page 1 of 1
APPLICATION NO. : 08/880745
DATED : October 12, 1999
INVENTOR(S) : Toshihiko Ashikari et al.

It is certified that error appears in the above-identified patent and that said Letters Patent is hereby corrected as shown below:

Column 23, line 25: "which in at" should read --which is at--.

Signed and Sealed this

Twenty-second Day of May, 2007

JON W. DUDAS
*Director of the United States Patent and Trademark Office*